United States Patent
DeBold

(10) Patent No.: US 6,960,472 B2
(45) Date of Patent: Nov. 1, 2005

(54) MONOCLONAL ANTIBODIES AGAINST N-TERMINUS PROBNP

(75) Inventor: Adolfo J. DeBold, Ottawa (CA)

(73) Assignee: Ottawa Heart Institute Research Corporation, Ontario (CA)

(*) Notice: Subject to any disclaimer, the term of this patent is extended or adjusted under 35 U.S.C. 154(b) by 341 days.

(21) Appl. No.: 10/359,046

(22) Filed: Feb. 4, 2003

(65) Prior Publication Data
US 2004/0096439 A1 May 20, 2004

Related U.S. Application Data

(63) Continuation of application No. 10/299,606, filed on Nov. 18, 2002, now abandoned.

(51) Int. Cl.⁷ .......................... C07K 16/26; C12N 5/20; C12N 5/18
(52) U.S. Cl. .................. 435/336; 435/332; 435/335; 435/337; 435/346; 435/353; 530/388.2; 530/388.23; 530/388.24; 530/388.25
(58) Field of Search .................. 530/388.2, 388.23, 530/388.24, 388.25; 435/332, 335, 336, 337, 346, 353

(56) References Cited

U.S. PATENT DOCUMENTS 5,786,163 A * 7/1998 Hall .......................... 435/7.92

* cited by examiner

Primary Examiner—Ronald B. Schwadron
(74) Attorney, Agent, or Firm—McHale & Slavin, P.A.

(57) ABSTRACT

Monoclonal antibodies having high affinity for N-terminus pro brain natriuretic peptide (NT-proBNP) are described. The monoclonal antibodies are prepared against a synthetic peptide having the Sequence ID No. 1. Specifically, the monoclonal antibodies described are produced from two hybridoma cell lines, 6G11-F11-D12 and 1C3-E11-R9, deposited with the American Type Culture Collection under Accession Numbers PTA-4844 and PTA-4845 respectively. The monoclonal antibody antibodies can be used as reagents in an immunoassay system to identify blood, serum or plasma levels of NT-proBNP. Such an immunoassay system can be used for diagnosing and quantifying congestive heart failure (CHF).

4 Claims, 2 Drawing Sheets

SEQUENCE LISTING

<160> NUMBER OF SEQ ID NOS: 1

<210> SEQ ID NO 1
<211> LENGTH: 25
<212> TYPE: PRT
<213> ORGANISM: Homo sapiens

<400> SEQUENCE: 1

His Pro Leu Gly Ser Pro Gly Ser Ala Ser Asp Leu Glu Thr Ser Gly
1               5                   10                  15

Leu Gln Glu Gln Arg Asn His Leu Gln
            20                  25

MONOCLONAL ANTIBODIES AGAINST N-TERMINUS PROBNP

CROSS REFERENCE TO RELATED APPLICATIONS

This application is a continuation of Ser. No. 10/299,606, filed on Nov. 18, 2002 now abandoned, the contents of which are herein incorporated by reference.

FIELD OF INVENTION

This invention relates to a monoclonal antibody which demonstrates specific binding to human N-Terminus proBNP (NT-proBNP); and particularly relates to hybridoma cell lines, designated as 6G11-F11-D12 (ATCC PTA-4844) and 1C3-E11-H9 (ATCC PTA-4845) and the monoclonal antibodies produced by each respectively. The monoclonal antibody of the present invention can be used for determining blood, serum or plasma levels of NT-proBNP. The antibody is particularly useful for rapid format diagnostic tests for diagnosing congestive heart failure.

BACKGROUND AND PRIOR ART

B-type natriuretic peptide (Brain natriuretic peptide, BNP) belongs to the family of structurally similar, but genetically distinct natriuretic peptides (NPs) first described by de Bold et al. (de Bold A J. Heart atria granularity: effects of changes in water-electrolyte balance. Proc Soc Exp Biol Med 1979; 161:508–511; de Bold A J, Borenstein H B, Veress A T and Sonnenberg H. A rapid and potent natriuretic response to intravenous injection of atrial myocardial extracts in rats. Life Sci 1981; 28:89–94).

The NPs possess potent diuretic, natriuretic and vasodilatory properties and have been reported as valuable diagnostic and prognostic markers in cardiovascular disease, particularly for patients in New York Heart Association (NYHA) classes I-IV congestive heart failure (CHF) (Boomsma F and van den Meiracker A H. Plasma A- and B-type natriuretic peptides: physiology, methodology and clinical use. Cardiovasc Res 2001; 51:442–449).

The BNP gene encodes for a 108 amino acid residue precursor molecule, proBNP. Prior to secretion by cardiomyocytes, cleavage of this prohormone results in the generation of bioactive BNP from the COOH terminus. In 1995, Hunt et al. (Hunt P J, Yandle T G, Nicholls M G, Richards A M and Espiner E A. The Aminoterminal Portion of Probrain Natriuretic Peptide (Probnp) Circulates In Human Plasma. Biochem Biophys Res Commun 1995; 14:1175–1183; Hunt P J, Richards A M, Nicholls M G, Yandle T G, Doughty R N and Espiner E A. Immunoreactive Amino-Terminal Pro-Brain Natriuretic Peptide (NT-PROBNP): A New Marker Of Cardiac Impairment. Clin Endocrinol 1997; 47:287–296) demonstrated that fragments corresponding to the N-terminal portion of the cleaved prohormone, NT-proBNP, also circulated in plasma, and like BNP, were a potentially important, and possibly more discerning, marker of ventricular dysfunction.

Many studies have demonstrated the clinical utility of measuring plasma concentrations of NPs, including NT-proBNP. NPs have been suggested as the biomarkers of choice for diagnosis and risk stratification of patients with heart failure (Clerico A, Del Ry S and Giannessi D. Measurement Of Cardiac Natriuretic Hormones (Atrial Natriuretic Peptide, Brain Natriuretic Peptide, And Related Peptides) In Clinical Practice: The Need For A New Generation Of Immunoassay Methods. Clin Chem 2000; 46:1529–1534; Mair J, Hammerer-Lercher A and Puschendorf B. The Impact Of Cardiac Natriuretic Peptide Determination On The Diagnosis And Management Of Heart Failure. Clin Chem Lab Med 2001; 39:571–588; Sagnella G A. Measurement And Importance Of Plasma Brian Natriuretic Peptide And Related Peptides. Ann Clin Biochem 2001; 38:83–93; Selvais P L, Donckier J E, Robert A, Laloux O, van Linden F, Ahn S, Ketelslegers J M and Rousseau M F. Cardiac Natriuretic Peptides For Diagnosis And Risk Stratification In Heart Failure: Influences Of Left Ventricular Dysfunction And Coronary Artery Disease On Cardiac Hormonal Activation. Eur J Clin Invest 1998; 28:636–642; McDonagh T A, Cunningham A D, Morrison C E, McMurray J J, Ford I, Morton J J and Dargie H J. Left Ventricular Dysfunction, Natriuretic Peptides, And Mortality In Urban Population. Heart 2001; 86:21–26). Several studies have shown the utility of using NP measurements to identify patients with left ventricular dysfunction, even amongst patients who are asymptomatic (i.e. NYHA class I) and it has been suggested that NP measurements as a screening tool may help effectively target patients within high risk heart failure groups (e.g. coronary artery disease, hypertension, diabetes, aged) who will require follow-up assessment and treatment (Hughes D, Talwar S, Squire I B, Davies J E and Ng L L. An Immunoluminometric Assay For N-Terminal Pro-Brain Natriuretic Peptide: Development Of A Test For Left Ventricular Dysfunction. Clin Sci 1999; 96:373–80; Omland T, Aakvaag A, Vik-Mo H. Plasma Cardiac Natriuretic Peptide Determination As A Screening Test For The Detection Of Patients With Mild Left Ventricular Impairment. Heart 1996; 76:232–237; McDonagh T A, Robb S D, Murdoch D R, Morton J J, Ford I, Morrison C E, et al. Biochemical Detection Of Left-Ventricular Systolic Dysfunction. Lancet 1998; 351:9–13; Schulz H, Langvik T A, Lund Sagen E, Smith J, Ahmadi N and Hall C. Radioimmunoassay For N-Terminal Probrain Natriuretic Peptide In Human Plasma. Scand J Clin Lab Invest 2001; 61:33–42; Talwar S, Squire I B, Davies J E, Barnett D B and Ng L L. Plasma N-Terminal Pro-Brain Natriuretic Peptide And The ECG In The Assessment Of Left-Ventricular Systolic Dysfunction In A High Risk Population. Eur Heart J 1999; 20:1736–1744; Hystad M E, Geiran O R, Attramadal H, Spurkland A, Vege A, Simonsen S and Hall C. Regional Cardiac Expression And Concentration Of Natriuretic Peptides In Patients With Severe Chronic Heart Failure. Acta Physiol Scand 2001; 171:395–403; Hobbs F D R, Davis R C, Roalfe A K, Hare R, Davies M K and Kenkre J E. Reliability Of N-Terminal Pro-Brain Natriuretic Peptide Assay In Diagnosis Of Heart Failure: Cohort Study In Representative And High Risk Community Populations. B M J 2002; 324:1498). NPs have been shown to have good prognostic value with regards to both morbidity and mortality in heart failure. Several studies have also demonstrated the utility of NP measurements in the prediction of left ventricular dysfunction and survival following acute myocardial infarction (Richards A M, Nicholls M G, Yandle T G, Frampton C, Espiner E A, Turner J G, et al. Plasma N-Terminal Pro-Brain Natriuretic Peptide And Adrenomedullin. New Neurohormonal Predictors Of Left Ventricular Function And Prognosis After Myocardial Infarction. Circulation 1998; 97:1921–1929; Luchner A, Hengstenberg C, Lowel H, Trawinski J, Baumann M, Riegger G A J, et al. N-Terminal Pro-Brain Natriuretic Peptide After Myocardial Infarction. A Marker Of Cardio-Renal Function. Hypertension 2002; 39:99–104; Campbell D J, Munir V, Hennessy O F and Dent A W. Plasma Amino-Terminal Pro-Brain Natriuretic Peptide Levels In Subjects Presenting To The Emergency Department With Suspected Acute Coronary Syndrome: Possible Role In Selecting Patients For Follow Up? Intern Med J 2001; 31:211–219; Nilsson J C, Groenning B A, Nielsen G, Fritz-Hansen T, Trawinski J. Hildebrandt P R, et al. Left Ventricular Remodeling In The First Year After Acute Myocardial Infarction And The Predictive Value Of N-Terminal Pro Brain Natriuretic Peptide. Am Heart J 2002; 143:696–702). Monitoring NP levels may also provide guidance in tailoring therapies to meet the required intensity of the individual patient and in monitoring therapeutic efficacy (Richards A M, Doughty R, Nicholls G, MacMahon S, Sharpe N, Murphy J, et al. Plasma N-Terminal Pro-Brain Natriuretic Peptide And Adrenomedullin. Prognostic Utility And Prediction Of Benefit From Carvedilol In Chronic Ischemic Left Ventricular Dysfunction. J Am Coll Cardiol 2001; 37:1781–1787; Troughton R W, Frampton C M, Yandle T G, Espiner E A, Nicholls M G and Richards A M. Treatment Of Heart Failure Guided By Plasma Aminoterminal Brain Natriuretic Peptide (N-BNP) Concentrations. Lancet 2000; 355:1126–30).

PRIOR ART

WO 93/24531 (U.S. Pat. No. 5,786,163) to Hall describes an immunological method of identifying N-terminal proBNP and the antibodies used for it. To obtain these antibodies single synthetically produced peptides from the sequence of N-terminal proBNP are used. The production of antibodies by means of peptide immunization is possible in principle but the affinity regarding the whole molecule generally is too low to reach the necessary sensitivity in a test procedure. In addition, there is a danger that when using peptides the antibodies obtained can for example identify the C-terminus of the peptide and can therefore only bind to this fragment of the whole molecule, thus resulting in antibodies which generally cannot bind to the whole molecule, or can do so to only a limited extent. In WO 93/24531 an antibody against one single peptide derived from the N-terminal proBNP is produced. It is shown that the antibodies produced bind to the immunization peptide (amino acids 47–64) in the competitive test format. It is however not shown that the antibodies are able to bind to native N-terminal proBNP as a whole molecule in a sample. Additionally, the sandwich test described in WO 93/24531 in a sample cannot be performed as described since there was no appropriate standard material and no antibodies against two different epitopes. Additionally, the competitive test performed in PTO 93/24531, where the peptide 47–64 competes in a labelled form as a tracer with a sample or the unlabelled peptide standard 47–64 to bind to polyclonal antibodies from rabbit serum, suffers from the fact that only a very moderate competition is reached after 48 hours of incubation from which only a low detection limit of approx. 250 fmol/ml can be derived. This is neither sufficient for the differentiation of healthy individuals and patients suffering from heart failure nor for a differentiated classification of patient samples into the severity degrees of heart failure. In addition, the long incubation times of the competitive test are not acceptable for routine measurements of the samples in automated laboratories.

Hunt et al. (Clinical Endocrinology 47 (1997), 287–296) also describes a competitive test for the detection of N-terminal proBNP. For this a complex extraction of the plasma sample is necessary before the measurement; this may lead to the destruction of the analyte and error measurements. The antiserum used is produced analogously to WO 93/24531 by immunization with a synthetic peptide—Hunt et al. produces the antiserum by immunization with the N-terminal proBNP amino acids 1–13 and the peptide of amino acids 1–21 is used as a standard. For this test long incubation times are necessary too. After an incubation of 24 hours a lower detection limit of 1.3 fmol/ml is reached.

WO 00/45176, Method of Identifying N-Terminal proBNP, Karl et al., discloses monoclonal and polyclonal antibodies isolated via the use of a recombinant NT-proBNP immunogen. The reference suggests the formation of an assay using the disclosed antibodies as being specific for NT-proBNP in bodily fluids. As will be more fully described, a comparison of the area under the curve (AUC) of a plot of the Receiver Operated Characteristics (ROC) for this assay versus the assay of the instant invention indicates that the instant invention demonstrates superior diagnostic performance.

WO 00/35951, Natriuretic Peptide Fragments, is directed toward an assay for NT-proBNP utilizing two antibodies directed toward differing epitopes of the NT-proBNP sequence. This assay suffers from similar deficiencies as that of Hall (U.S. Pat. No. 5,786,163) in that the antibodies are raised against synthetic peptide fragments as the immunogen.

There remains a need for a human HUMAN nt-PRObnp monoclonal antibody that manifests high affinity and sensitivity for incorporation in an immunoassay system that can be used for diagnosing and quantifying congestive heart failure according to a rapid format procedure such as that which is disclosed in U.S. Pat. No. 5,559,041.

SUMMARY OF THE INVENTION

The limitations of the prior art are addressed in the present invention by providing a monoclonal antibody that is specific for NT-proBNP, particularly to the polypeptide consisting of amino acids 1–25 thereof. According to one embodiment of this invention, there is provided a hybridoma cell line 6G11-F11-D12. According to a further embodiment of this invention, there is provided a hybridoma cell line 1C3-E11-H9. The monoclonal antibodies produced from these hybridoma recognize an epitope present within the amino acid residues 1–25 of the native NT-proBNP molecule. These monoclonals were produced from supernatants for use in an NT-proBNP ELISA in pairing with Goat Polyclonal Antibodies, and the ELISA assays and rapid format device are the subject of U.S. Ser. No. 10/300,733 now abandoned to Davey et al and U.S. Ser. No. 10/299,583 to Kang et al respectively, which applications are filed on even date herewith, the contents of which are herein incorporated by reference. The hybridoma cell lines 6G11-F11-D12 and 1C3-E11-H9 were deposited, in accordance with the Budapest Treaty, with the American Type Culture Collection, 10801 University Blvd., Manassas, Va. 20110-2209 on Dec. 5, 2002 under Accession Numbers PTA-4844 and PTA-4845 respectively. In accordance with 37 CFR 1.808, the depositors assure that all restrictions imposed on the availability to the public of the deposited materials will be irrevocably removed upon the granting of a patent. The depositors additionally assure that the deposited materials will be replaced if viable samples cannot be dispensed by the depository.

The monoclonal antibody of the present invention can be distinguished from the antibodies known in the art in that they are characterized for their diagnostic value due to their specificity and sensitivity for NT-proBNP and for their high affinity for NT-proBNP.

Methods for preparing synthetic peptides are well known in the art and have been described in detail in the following references (C. Y. Wang et al., Science 254, 285–288, 1991; G. W. McLean et al., Journal of Immunological Methods, 137, 149–157, 1991 or P. D. Nicol et al., The Journal of Nuclear Medicine, 34, 2144–2151. 1993). A single peptide chain is usually not very immunogenic in experimental animals, and it is generally necessary to couple the peptide to a carrier protein such as KLH or bovine serum albumin. However, antisera produced using protein-conjugated peptides are often low in titre. An approach to produce antisera against synthetic peptides has been described by D. N. Posnett et al. (J. Biol. Chem. 263, 1719, 1988); J. P. Tam (Proc. Natl. Acad. Sci., U.S.A., 85, 5409, 1988); and G. W. McLean, et al. (J. Immunol. Methods, 137, 149, 1991). The alpha and epsilon amino groups on lysine were used to synthesize a multiple branching polylysine core onto which the peptide of interest was synthesized.

DETAILED DESCRIPTION OF THE INVENTION

The present invention provides monoclonal antibodies secreted by hybridomas herein designated as 6G11-F11-D12 and as 1C3-E11-H9 for use in a method of immunoassay being antibodies specific to the polypeptide consisting of amino acids 1–25 (SEQ ID NO: 1) of human N-terminal brain natriuretic factor BNP (1–25). The said antibodies may be used for research in general and for diagnostic purposes in human clinical entities.

Production of monoclonal antibodies:
1) Immunogen. A chemically synthesized peptide with the sequence ID NO:1 shown above with an added C-terminal Cys was synthesized by Advanced ChemTech (5609 Fern Valley Road, Louisville Ky. 40228-1075 USA). The peptide was coupled to keyhole limpet hemocyanin (KLH) using an IMJECT Maleidimide reagent kit (Pierce, 37487 N. Meridian Road, Rockford, Ill. 61105).
2) Immunization. The KLH-peptide complex equivalent to 25 micrograms of peptide/animal combined with Freund's adjuvant (Sigma Chemical Co., St Louis Mo.), was injected intramuscularly into Balb/c mice for priming. Other adjuvants may be used. Complex equivalent to 12 micrograms of peptide was injected in the same manner every three weeks for boosting of titer. Bleeds were carried out for titer determination four days after each boosting.
3) Titer determination in mice. Serum samples obtained thrice from each immunized mice were used for titer determination as follows. Microtiter plate wells were coated—with peptide solution (1 ug/ml in phosphate buffered saline (PBS), 0.9% NaCl buffer) at 50 ul/well 12–24 hours. Followed by washes with PBS containing 0.05% Tween-20 and saturation with PBS containing 1% bovine serum albumin (BSA).

Mouse sera dilutions are added to wells (100 microliters/well). Each serum was tested at the following dilutions: $1/100$, $1/10^3$, $1/10^4$, $1/10^5$, $1/10^6$, and $1/10^7$ in PBS containing 0.1BSA and 0.02% $NaN_3$. After washing, 50 microliters/well of detection conjugate (Goat anti-mouse horseradish peroxidase conjugated) at a dilution of 1/5000.

After washing a chromogenic reaction is carried out using freshly prepared solution (at a ratio of 1:1 TME buffer to hydrogen peroxide solution) at 100 ul/well and is incubate for approximately 5 minutes. The reaction is stopped by adding to each well 100 microliters of 2.5M $H_2SO_4$ and read at 450 nm in a plate reader.

The data for mouse No. 60 from which the hybridomas 6G11 and as 1C3 were derived are shown below.

Figure 1:
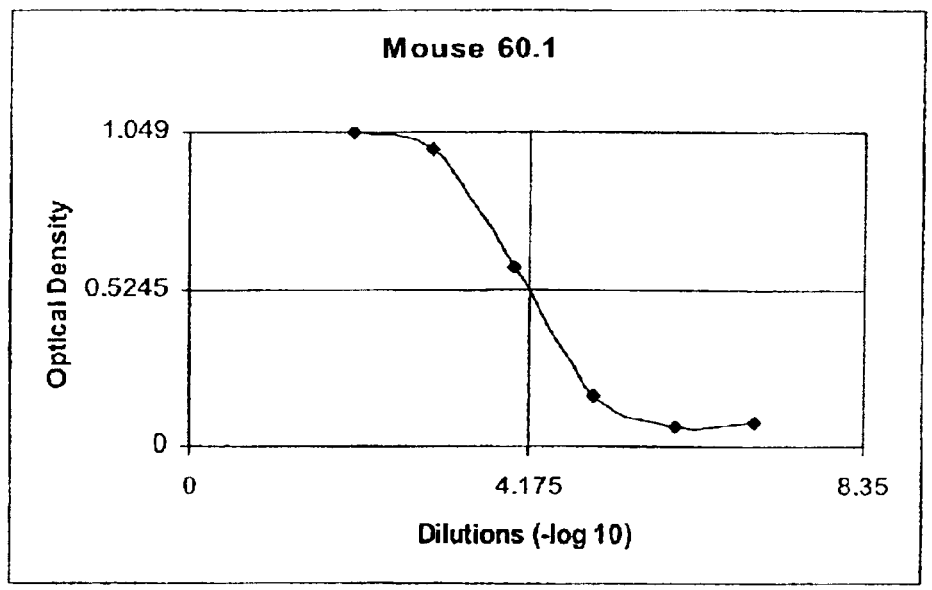
FIG. 1 references Bleed No. 1 for Mouse 60.
Figure 2:
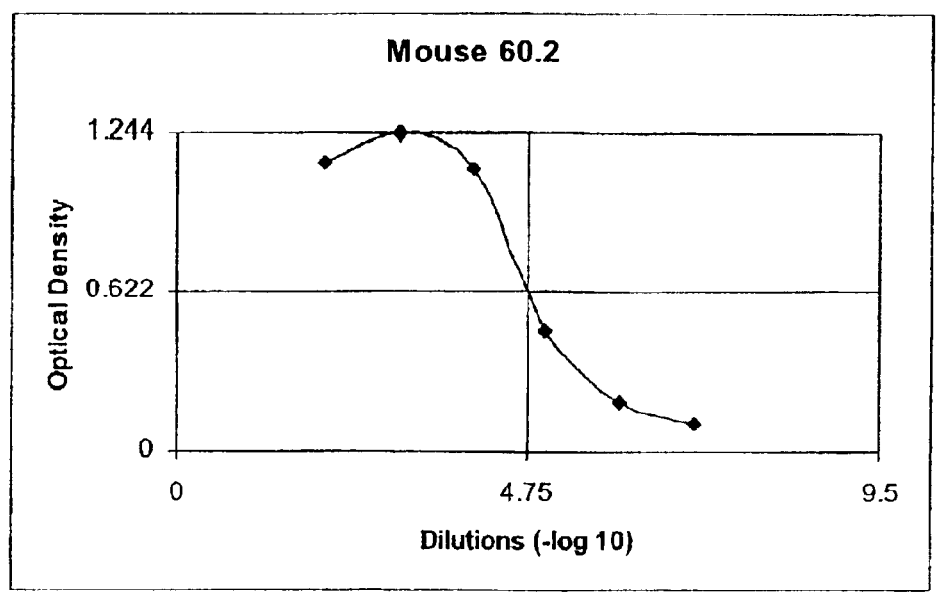
FIG. 2 references Bleed No. 2 for Mouse 60.
Figure 3:
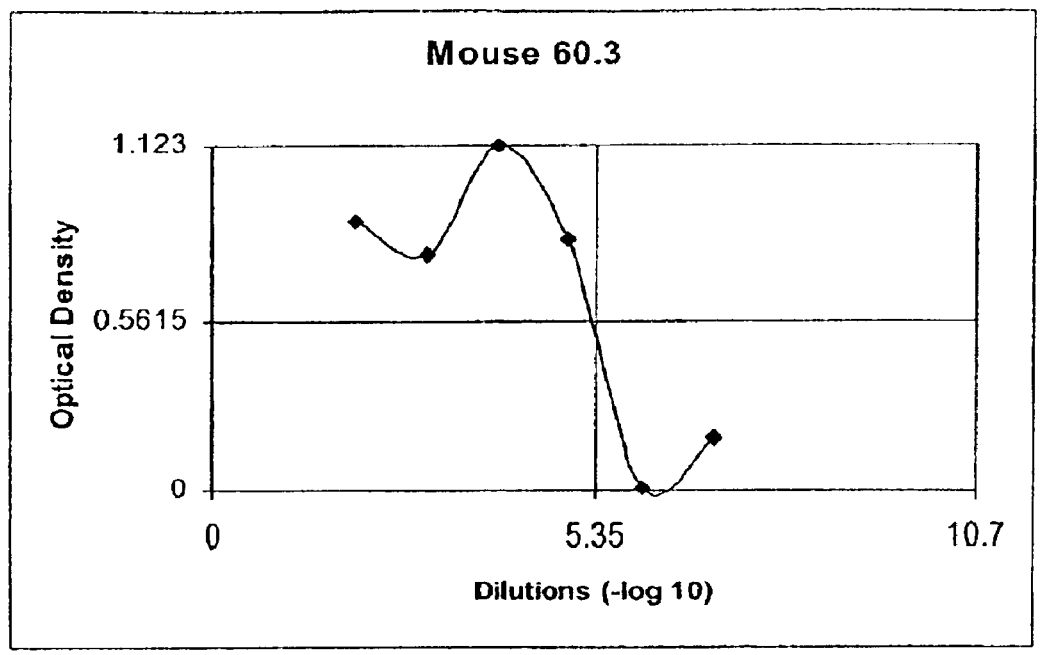
FIG. 3 references Bleed No. 3 for Mouse 60.

Bleed No. 1. Titer=4.175 is referenced in FIG. 1.
Bleed No. 2. Titer=4.75 is referenced in FIG. 2.
Bleed No. 3. Titer=5.35 is referenced in FIG. 3.
4) Preparation of hybridomas.
4a) Isolation of splenocytes. The animals are rendered unconscious in a $CO_2$ chamber, sacrificed by cervical dislocation and immersed in 70% ethanol. Under sterile conditions the spleen is removed and transferred to a sterile centrifuge tube containing 10 mls Dulbecco's supplemented culture medium. A suspension of cells is obtained by transferring the spleen to a culture dish with Dulbecco's culture medium and gently pressing with the plunger of a sterile 5 cc syringe plunger and passing the material through a 50-mesh cell strainer. The procedure is repeated three times. The suspension is centrifuged and the cell pellet is resuspended in red blood cell lysis buffer. After incubation and addition of Dulbecco's culture medium the cells are centrifuged twice more and are suspended in the same medium in which an estimate of cell density is made by standard cell counting.
4b) Preparation of Plasmacytoma Cells. SP2/0-AG14 non secreting, mouse plasmacytoma cells in a mid-logarithmic growth phase are harvested from previously developed culture flasks, centrifuged three times in cell culture medium and resuspended in cell culture mediun obtaining the number of viable cells as previously done for splenocytes.
4c) Cell Fusion. Spleenocytes and plasmacytoma cells are combined at approximately 1:1 ratio in a 15 ml sterile centrifuge tube and centrifuged at 1500 rpm for 10 minutes discarding the supernatant. Fusion medium (50% polyethylene glycol in supplemented medium—no FBS), 0.5 ml is added and gently resuspending the cell pellet with the pipette tip.

Supplemented medium (5 ml) no FBS, is added slowly to create a delicate vortex of the cell suspension with the pipette tip. Finally, 3.5 mls of Dulbecco's supplemented medium containing 25% fetal bovine serum is added slowly 'over 3 minutes'.

The cell mixture is placed into approx. 70ml of Dulbecco's supplemented medium containing 25% FBS and the 1X HAT components to select for fused cells (10 μM hypoxanthine, 0.4 μM aminopterin and 16 μM thymidine). One hundred microlites of the cell suspension is placed into each of 96 wells of culture plates and maintained at 37° C. in a carbon dioxide incubator.

Approximately 4–5 days after inoculation of the 96-well plates, the cells are fed by adding to each well 100–150 μL of supplemented Dulbecco's medium containing 100 μM hypoxanthine, 0.4 μM aminopterin and 16 μM thymidine, and 20% FBS—(DMEM 20% FBS, 1XHT).

Cell cloning is subsequently achieved by serial dilutions. Typical ELISA results obtained in the last phase of cloning for clones 1C3-E11-H9 and 6G11-F11-D12 using the technique described above for screening mouse sera are:

|  | OD | Blank |
|---|---|---|
| 1C3-E11-H9 | 1.068 | 0.6 |
| 6G11-F11-D12 | 0.9 | 0.26 |

5) Ascites production. Monoclonal antibody quantities suitable for research or clinical assay development are obtained by injection of the hybridomas into the peritoneal cavity of mouse or other suitable preparation either in vivo or in vitro.

Ascites fluid containing antibodies produced by clones 1C3-E11-H9 and 6G11-F11-D12 was obtained by injecting mice with pristine 10–15 days prior to use. Approximately $2-4 \times 10^6$ hybridoma cells are injected into the peritoneal cavity. Seven to 10 days after injection the ascites fluid is collected under sterility. The fluid is let to clot and cleared by centrifugation. EDTA (60 microliters of 5% EDTA, pH 7.2, is added and the fluid is incubated for one hour at 37° C. and then frozen at −20° C.

6) Isotyping of NT-proBNP Monoclonal Antibodies. Isotyping of the monoclonal antibodies was performed using a Mouse Typer® SubIsotyping Kit (BioRad) following the manufacturer's recommendations. Briefly, monoclonal antibodies in confluent hybridoma supernatants were capture via donkey anti-mouse $IgG_{(H+L)}$ immunoglobulins (Jackson ImmunoResearch) immobilized on the surface of a 96-well microtiter plate (NUNC, MaxiSorp, GIBCO BRL). 50 μl per well of culture supernatant was used. Following incubation for 1 hour at 37° C. in a $CO_2$ incubator, the plate was washed with PBS containing 0.05% (v/v) Tween 20. One hundred microliters of each rabbit anti-mouse panel reagent from the Mouse Typer® SubIsotyping Kit was added to the appropriate wells and incubated for 1 hour at room temperature (RT) on a shaker. After washing the plate, 100 microliters/well peroxidase conjugated donkey anti-rabbit IgG immunoglobulins (Jackson ImmunoResearch) were added and incubated for 1 hour at room temperature on a shaker. Following a wash step, TMB substrate solution (Moss) was added to the plate. After 5 minutes incubation at RT in the dark, the reaction was stopped with 1 N $H_2SO_4$ and optical density read at $450_{nm}$.

The following results were obtained:
1C3-E11-H9=k, IgG1>IgG3
6G11-F11-D12=k, IgG1>IgG3

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A hybridoma cell line 6G11-F11-D12, deposited with American Type Culture Collection under Accession Number PTA-4844.

2. A monoclonal antibody produced from hybridoma cell line 6G11-F11-D12, deposited with American Type Culture Collection under Accession Number PTA-4844.

3. A hybridoma cell line 1C3-E11-H9, deposited with American Type Culture Collection under Accession Number PTA-4845.

4. A monoclonal antibody produced from hybridoma cell line 1C3-E11-H9, deposited with American Type Culture Collection under Accession Number PTA-4845.

* * * * *